United States Patent [19]

Fenical et al.

[11] Patent Number: 5,688,783
[45] Date of Patent: Nov. 18, 1997

[54] SALINAMIDES

[75] Inventors: William H. Fenical, Del Mar; Robert S. Jacobs, Santa Barbara; Paul R. Jensen, San Diego, all of Calif.

[73] Assignee: The Regents of the University of California, Oakland, Calif.

[21] Appl. No.: 552,841

[22] Filed: Nov. 3, 1995

Related U.S. Application Data

[62] Division of Ser. No. 186,789, Jan. 25, 1994.

[51] Int. Cl.$^6$ .................. C07D 498/08; A61K 31/395
[52] U.S. Cl. .................. 514/183; 540/450; 530/317; 530/321
[58] Field of Search .................. 514/183

[56] References Cited

PUBLICATIONS

Trischman et al. "J. Am. Chem. Soc." vol. 116, pp. 757–758 (1994).

Primary Examiner—Robert T. Bond
Attorney, Agent, or Firm—Oppenheimer Poms Smith

[57] ABSTRACT

Salinamides A and B are disclosed. These two bicyclic depsipeptides are produced by fermentation of a specific marine actinomycete, a Streptomyces sp, (CNB-091) in saltwater-based media. Salinamides A and B are useful as anti-biotic and anti-inflammatory agents.

3 Claims, 5 Drawing Sheets a: -30° C b: 26° C

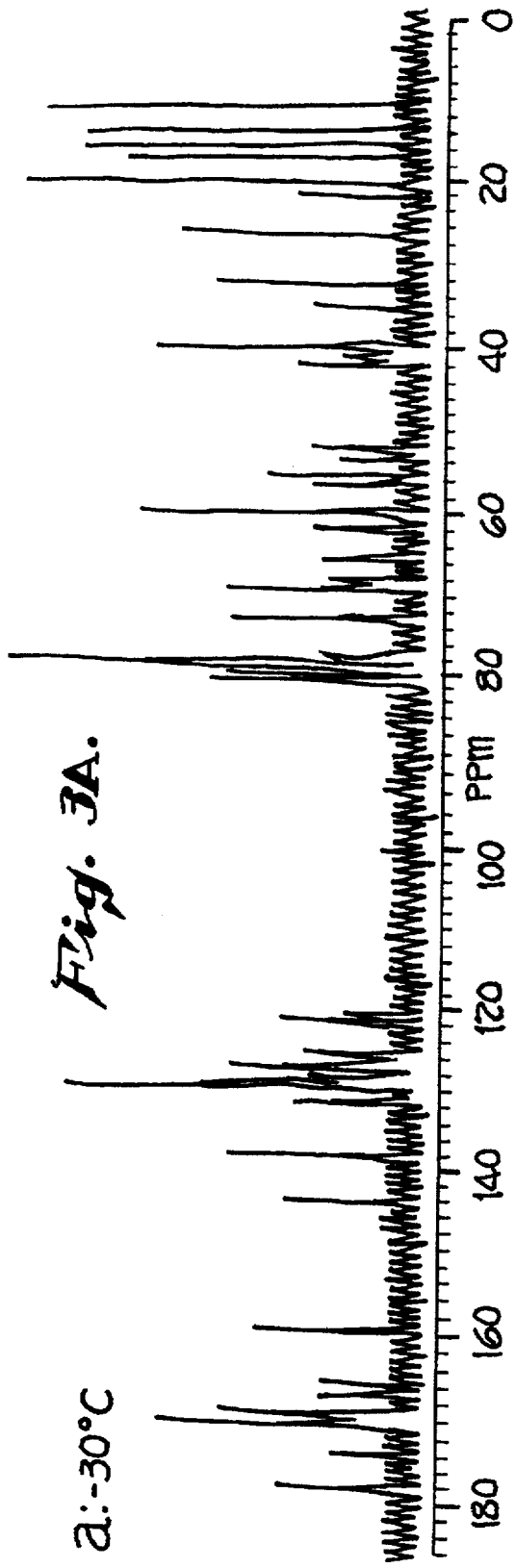
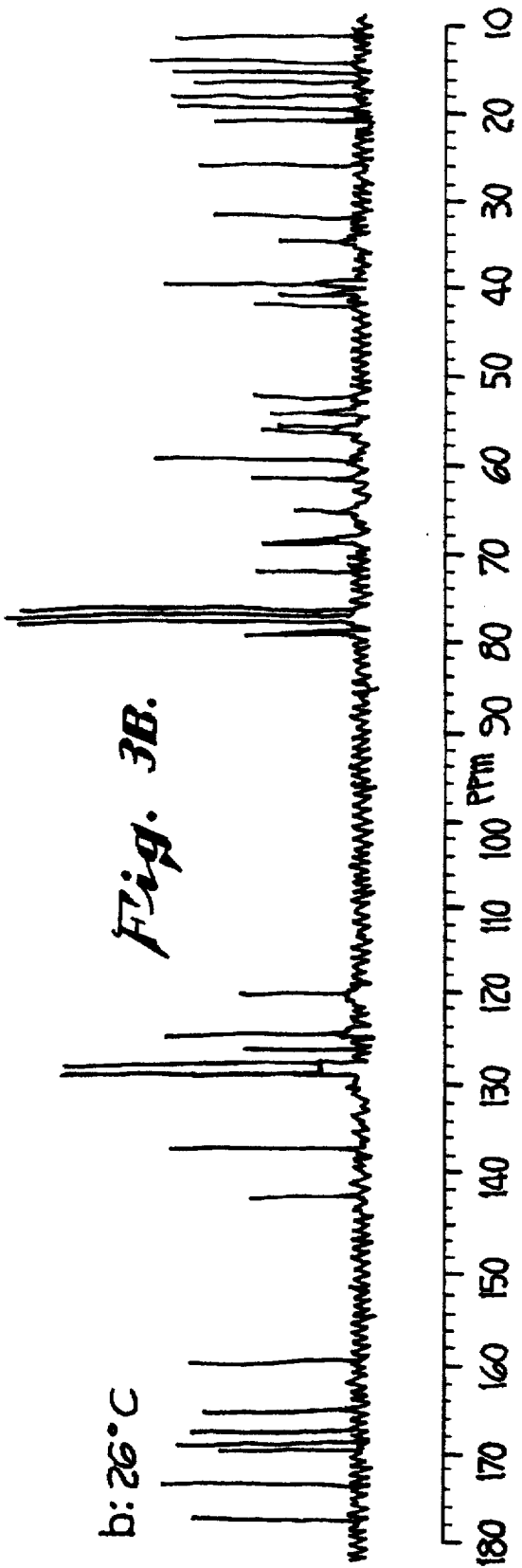
Fig. 3A. a: -30°C
Fig. 3B. b: 26°C

SALINAMIDES

This is a divisional of copending application Ser. No. 08/186,789 filed on Jan. 25, 1994.

This invention was made with Government support under Grant No. CA-44848, awarded by the National Institutes of Health. The Government has certain rights in this invention.

BACKGROUND OF THE INVENTION

1. Field of the Invention

The present invention relates generally to marine actinomycetes or filamentous bacteria which produce anti-biotics, anti-inflammatory agents and associated compounds. More particularly, the present invention relates to the discovery and isolation of a particular marine actinomycete which, when subjected to fermentation in seawater-based media, is capable of producing two bicyclic depsipeptides that are effective anti-biotic and anti-inflammatory agents.

2. Description of Related Art

There is a growing interest in investigating diverse classes of marine bacteria to determine their ability to produce secondary metabolites that are useful as drugs or pharmaceutical agents. Terrestrial actinomycetes are one type of bacteria which are known to produce a large number of antibiotic and associated compounds. Related bacteria are known to exist in various marine habitats including the surfaces of marine animals and plants (Fenical, W. *Chem. Rev.* 1993, 93, 1673–1683; Gil-Turnes, M. S., Hay, M. E., Fenical, W. *Science* 1989, 246, 116–118; and Gil-Turnes, M. S., Fenical, W. *Biol. Bull.* 1992, 182, 105–108). The actinomycetes are also found in shallow water marine sediments (see Jensen, P. R., Dwight, R., Fenical, W. *Appl. Environ. Microbiol.* 1991, 37, 1107–1108).

Some of the secondary metabolites produced by marine actinomycetes have been found to possess antibiotic properties. For example, see Pathirana, C., Jensen, P. R., Fenical, W. *Tetrahedron Lett.* 1993, 33, 7663–7666; Pathirana, C., Jensen, P. R., Dwight, R., Fenical, W. *J. Org. Chem.* 1992, 57, 740–742; and Okami, Y., Hopita, K., Yoshida, M., Ikoda, D., Kondo, S., Umozawa, H. *J. Antibiot.* 1979, 32, 964–966. Other secondary metabolites have been found to possess antitumor properties (see Tapiolas, D. M., Roman, M., Fenical, W., Stout, T. J., Clardy, J. *J. Am. Chem. Soc.* 1991, 115, 4682–4683; and Takahashi, A., Kurosawa, S., Ikeda, D., Okami, Y., Takeuchi, T. *J. Antibiot.* 1989, 42, 1556–1561).

Although some marine bacteria have been isolated which are capable of producing antibiotics and antitumor agents, there is a continuing need to discover and isolate additional marine bacteria that are capable of producing secondary metabolites which are useful as pharmaceutical agents. In addition, there is a continuing need to provide new methods for fermenting marine bacteria to optimize production of useful secondary metabolites.

SUMMARY OF THE INVENTION

In accordance with the present invention, a new marine actinomycete has been discovered and isolated from the surface of the jellyfish *Cassiopeia xamachana* which is commonly found in the Florida Keys. The actinomycete has been given the name CNB-091. It was discovered that fermentation of CNB-091 in seawater-based media resulted in the production of two secondary metabolites which are useful as anti-biotic and anti-inflammatory agents. The two secondary metabolites are bicyclic depsipeptides which have been identified as salinamide A and salinamide B.

Salinamide A has the structure

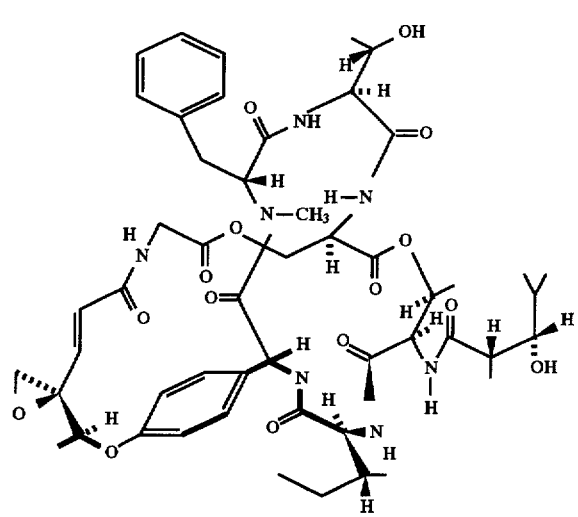

Salinamide B has the structure

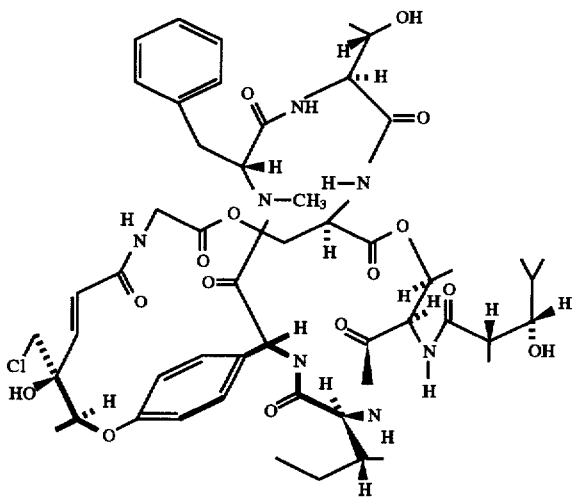

As a feature of the present invention, salinamide A and/or B may be used alone or in combination with a variety of pharmaceutical carriers to form compositions which are useful for treating inflammation of tissue. Salinamide A and/or B may also be combined with suitable pharmaceutical carriers to form compositions which may be used to treat bacterial infections. These antibiotic compositions are especially well-suited for inhibiting Gram-positive bacteria.

The above discussed and many other features and attendant advantages of the present invention will become apparent as the invention becomes better understood by reference to the following detailed description when taken in conjunction with the accompanying drawings.

3

BRIEF DESCRIPTION OF THE DRAWINGS

FIGS. 3A and 3B are $^{13}C$ NMR spectra of salinamide A taken at −30° C. and 26° C., respectively.

DESCRIPTION OF THE PREFERRED EMBODIMENTS

Figure 1:
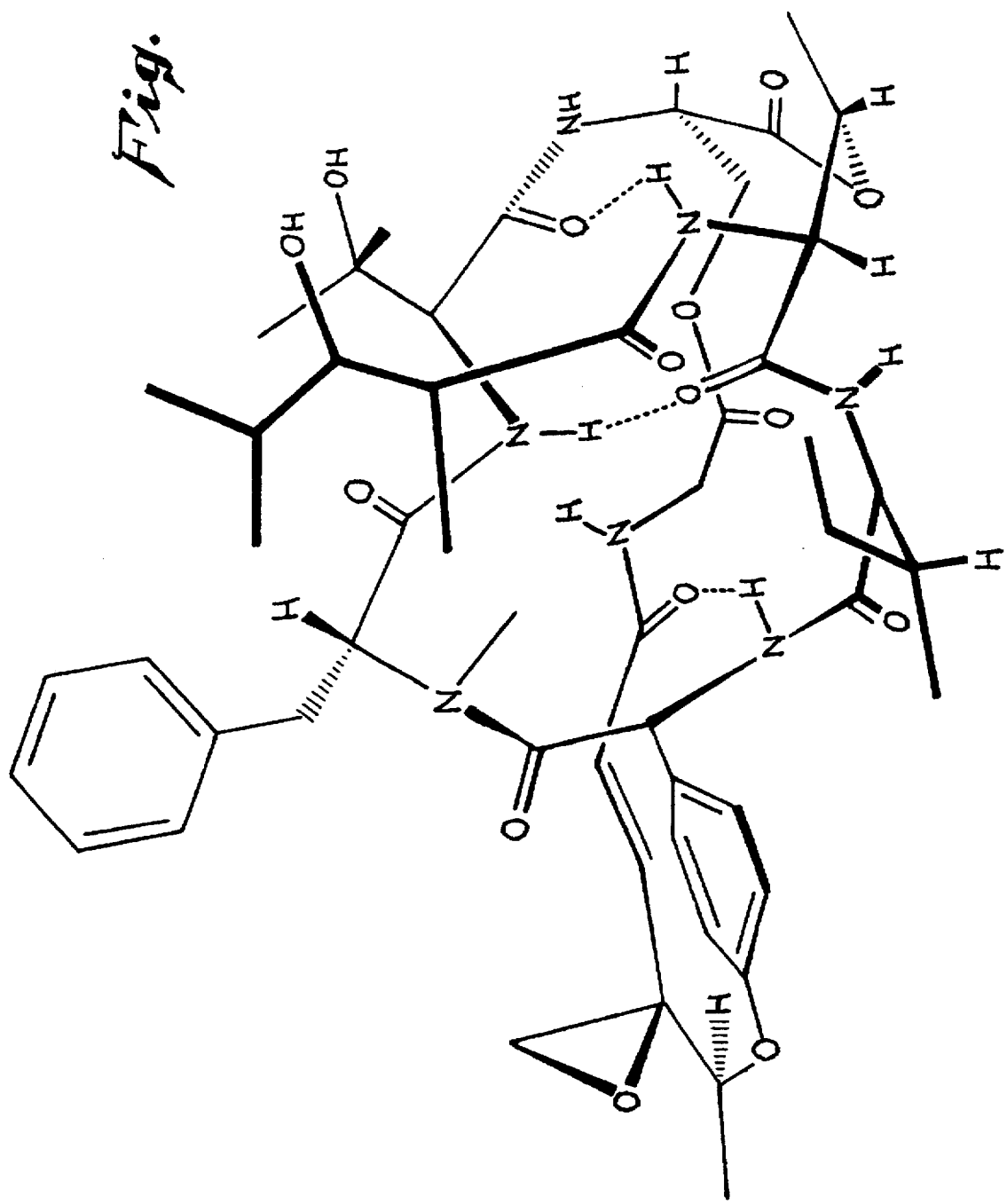
FIG. 1 is a three dimensional representation of the chemical structure of salinamide A.

The two new compounds discovered in accordance with the present invention are bicyclic depsipeptides. The two depsipeptides (salinamide A and salinamide B) are related as epoxide and chlorohydrin.

The structure of salinamide A is

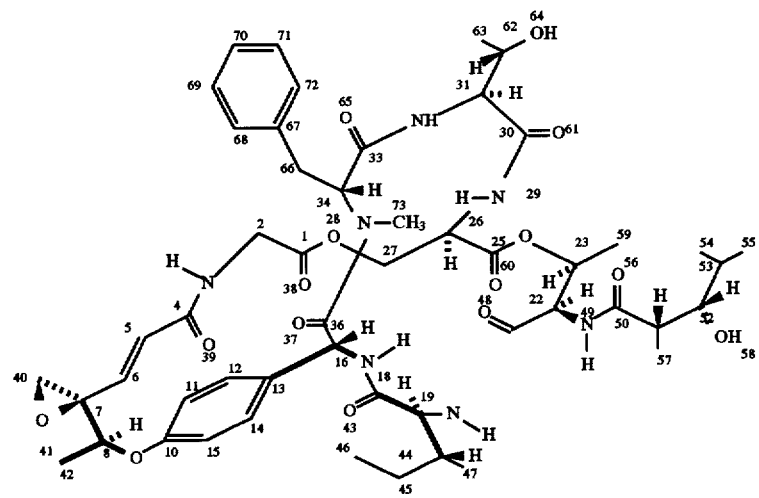

The spectral data for salinamide A is set forth in Table 1.

TABLE 1

Spectral Data for Salinamide A

Source: CNB091, a Streptomyces sp. from a surface swab of a *Cassiopeia xamachana*. Culture maintained at Scripps Institute of Oceanography, University of California at San Diego.

$[\alpha]_D^{26°}$ (c 0.97,CDCl$_3$)   mp 221–225° C. decomposes

Molecular Formula: $C_{51}H_{69}N_7O_{15}$

HRFABMS: (M + H$^+$) m/z 1020.492 (obs), 1020.493 (calc), Δ 1.0 ppm

IR (CDCl$_3$): 3436, 3379, 1745, 1735, 1682, 1657, 1636 cm$^{-1}$

UV (MeOH): 281, 267, 224, 208 nm

The NMR data for salinamide A is set forth in Table 2. The carbon numbers in Table 2 correspond to the numbered carbons in the above formula for salinamide A.

4

TABLE 2

NMR Data for Salinamide A

| C/X # | δ $^{13}C^a$ | δ $^1H^b$ | COSY$^c$/TOCSY$^d$ | HMBC$^d$ | ROESY$^d$ |
|---|---|---|---|---|---|
| 1 | 169.7 (C) | | | | |
| 2 | 40.8 (CH2) | 3.66 (d, 19.1) | 3 | 1, 4 | 19, 3, |
|   |   | 4.90 (dd, 19.1, 19.7) | 3 | 4 | (4.90) 3, (3.66) |
| 3 |   | 6.23 (d, 9.0) | 2 | 5 | 2, 5 |
| 4 | 165.3 (C) | | | | |
| 5 | 120.1 (CH) | 5.64 (d, 14.8) | 6 | 4, 6, 7 | |
| 6 | 142.9 (CH) | 6.21 (d, 14.8) | 5 | 4, 5, 7 | 5, 8, 40 |
| 7 | 59.6 (C) | | | | |
| 8 | 78.9 (CH) | 4.91 (q, 9.7) | | 7, 10, 42, 68 | 6, 42, 40, 11 72 |
| 10 | 159.3 (C) | | | | |
| 11 | 125.0† (CH) | 6.62 (br, 8) | | | |
| 12 | 127.9‡ (CH) | 6.82 (br, 8) | | | |
| 13 | 120.6 (C) | | | | |
| 14 | 130.8‡ (CH) | 6.82 (br, 8) | | | |
| 15 | 125.6‡ (CH) | 6.62 (br, 8) | | | |
| 16 | 56.4 (CH) | 5.17 (d, 3.2) | 17 | 11–15, 36 | 73, 57, 17, 32 |
| 17 |   | 8.41 (d, 3.2) | 16 | 18 | 19, 16, 44, 57 |
| 18 | 173.6 (C) | | | | |
| 19 | 53.6 (CH) | 5.05 (dd, 10.4, 4.0) | 44, 20 | 18, 21, 45, 47, 50 | 2, 47, 45, 20, 17 |
| 20 | | | | | |
| 21 | 167.5 (C) | | | | |
| 22 | 55.6 (CH) | 4.83 (dd. 9.7, 2.2) | 23, 49 | 50 | 59, 49, 20 |
| 23 | 72.4 (CH) | 5.45 (dq. 6.1, 2.2) | 22, 59 | | 59 |
| 25 | 168.6 (C) | | | | |
| 26 | 52.0 (CH) | 4.64 (m) | 27, 29 | | 27 |
| 27 | 65.6 (CH$_2$) | 4.66 (d, 10.8) | (4.42) | 25, 26 | 26, 29, (4.42) |
|   |   | 4.42 (dd, 10.8, 3.2) | (4.66) | | 26, 29, (4.66) |

TABLE 2-continued

NMR Data for Salinamide A

| C/X # | δ $^{13}$C$^a$ | δ $^1$H$^b$ | COSY$^c$/ TOCSY$^d$ | HMBC$^d$ | ROESY$^d$ |
|---|---|---|---|---|---|
| 29 | | 7.24 (bd, 6.1) | 26 | 1, 26, 27, 30 | 27 |
| 30 | 169.1 (C) | | | | |
| 31 | 61.3 (CH) | 4.32 (d, 7.2) | 32, 64 | | 33, 45, 73, 5 |
| 32 | | 7.21 (bd. 7.6) | | 33 | 16, 45, 73 |
| 33 | 168.9 (C) | | | | |
| 34 | 68.7 (CH) | 3.92 (dd, 11.2, 3.6) | 66 | | 73, 66 (3.34) |
| 36 | 169.9 (C) | | | | |
| 40 | 55.4 (CH$_2$) | 2.44 (d, 5.4) | (2.95) | 5, 6, 7 | 5, 6, 8 |
| | | 2.95 (d, 5.4) | (2.44) | 7 | 8, 42 |
| 42 | 14.1 (CH3) | 1.32 (d, 6.1) | | 7, 8 | 8, 40 (2.95) |
| 44 | 39.5 (CH) | 1.77 (m) | 19, 47, 45 | | 19, 47 |
| 45 | 26.1 (CH$_2$) | 1.14 (m, 7.0) | 44, 46, (1.28) | 19, 44 | |
| | | 1.28 (m, 6.5) | 46, (1.14) | | 19, 31, 62, 32 |
| 46 | 11.5 (CH$_3$) | 0.87 (d, 7.9) | 45 | | 45 |
| 47 | 14.2 (CH$_3$) | 0.83 (d, 7.2) | | 19, 44, 45 | 19, 44, 20 |
| 49 | | 7.95 (bd, 9.7) | 22 | 50 | 22, 51, 20 |
| 50 | 177.6 (C) | | | | |
| 51 | 41.6 (CH) | 2.76 (dq, 6.8, 4.3) | 52, 57 | | 52–55, 57, 63, 44, 64, 58 |
| 52 | 79.4 (CH) | 3.18 (bd, 7.0, 3.5) | 51, 53, 54, 55, 57, 58 | | 51, 54, 55, 57, 31, 58 |
| 53 | 32.2 (CH) | 1.62 (ddd, 7, 4.3, 3.2) | 52, 54, 55 | 52 | 51, 52, 54, 55, 64, 58 |
| 54 | 18.6 (CH$_3$) | 0.96 (d, 6.8) | 52, 53 | 52, 53 | 51, 52, 53, 58 |
| 55 | 19.7 (CH$_3$) | 0.88 (d, 6.5) | 52, 53 | 52, 53 | 51, 52, 53 |
| 57 | 16.7 (CH$_3$) | 1.38 (d, 6.8) | 51, 52 | 68, 72 | 16, 31, 62, 51, 52, 11, 20, 17, 64, 58 |
| 58 | | 3.46 (bd, 8.6) | 52 | | 51–54, 57, 63, 66, 64 |
| 59 | 15.6 (CH$_3$) | 1.30 (d, 6.1) | 23 | 23 | 23, 22 |
| 62 | 68.1 (CH) | 4.32 (m) | 63, 64 | | 45, 63, 57 32, 64 |
| 63 | 21.1 (CH$_3$) | 1.56 (d, 6.1) | 62, 64 | 31, 62, 66 | 62, 51, 64, 58 |
| 64 | | 5.84 (bd, 1.8) | 31, 62, 63 | 63 | 31, 73, 62, 63, 51, 53, 57, 58 |
| 66 | 34.6 (CH$_2$) | 3.34 (dd, 14.4, 3.6) | 34 | 34 | 34, 27, 66, 68, 58 |
| | | 3.63 (dd, 14.4, 3.6) | 34 | 34 | 34, 66, 15 |
| 67 | 137.1 (C) | | | | |
| 68,72 | 129.0 (CH) | 7.09 (bd, 5.0) | 66 | 34 | |
| 69,71 | 128.4 (CH) | 7.09 (bd, 5.0) | | | |
| 70 | 126.8 (CH) | 7.09 | | | |
| 73 | 40.1 (CH$_3$) | 2.67 (s) | | 36, 34 | 16, 34, 31, 68, 32, 64 |

$^a$Recorded in CDCl$_3$ at –30° C. on a VXR500 NMR at 125 MHz. Chemical shifts are reported with reference to internal TMS at 0.00 ppm.
$^b$Recorded in CDCl$_3$ at –30° C. on a VXR500 NMR at 500 MHz. Chemical shifts are reported with reference to internal TMS at 0.00 ppm.
$^c$Recorded in CDCl$_3$ at 26° C. on a Nicolet 360 MHz NMR.
$^d$Recorded in CDCl$_3$ at 26° C. on a VXR500 500 MHz NMR. Chemical shifts are reported with reference to CDCl$_3$ at 77.0 ppm for 13C shifts and internal TMS at 0.00 ppm for 1H shifts.
$^{†,‡}$Shifts may be interchanged.

Figure 2A:
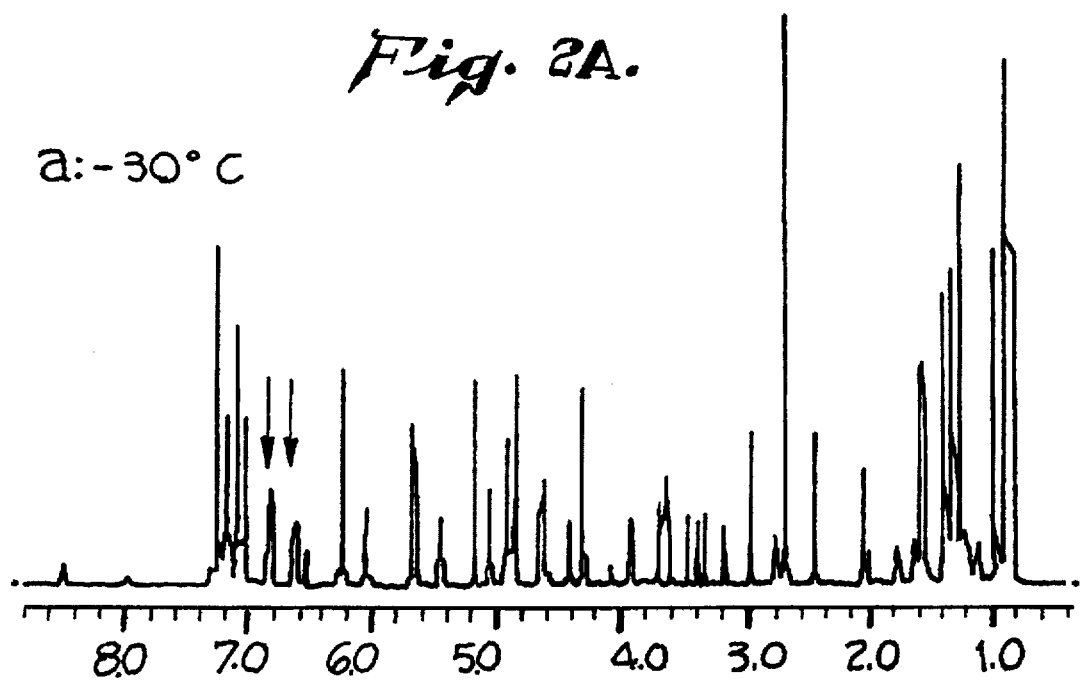
FIGS. 2A and 2B are NMR spectra of salinamide A taken at −30° C. and 26° C. respectively
Figure 2B:
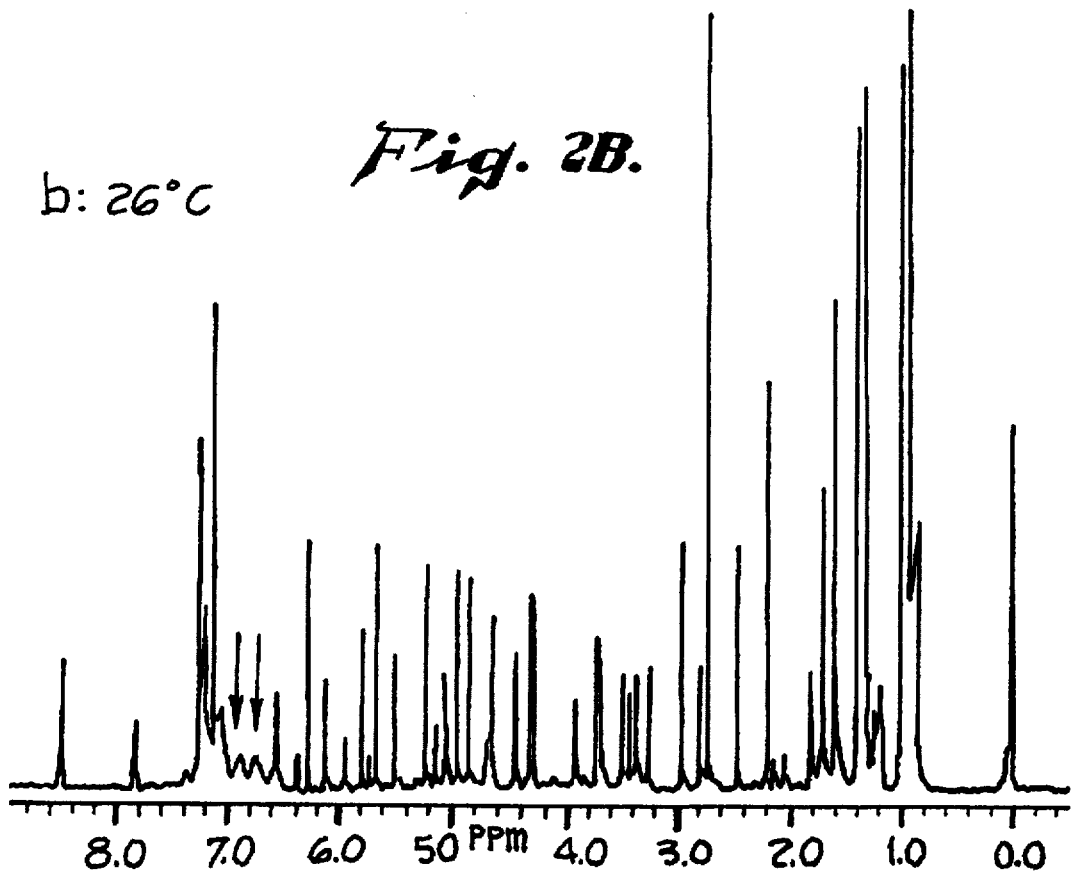

A three dimensional view of salinamide A is shown in FIG. 1. FIG. 2A is the NMR spectra of salinamide A in CDCl$_3$ at 500 MHz at –30° C. FIG. 2B is the NMR spectra of salinamide A in CDCl$_3$ at 500 MHz at 26° C. FIG. 3A is the $^{13}$C NMR spectra of salinamide A in CDCl$_3$ at 125 MHz at –30° C. FIG. 3B is the $^{13}$C NMR spectra of salinamide A in CDCl$_3$ at 125 MHz at 26° C.

The structure for salinamide B is

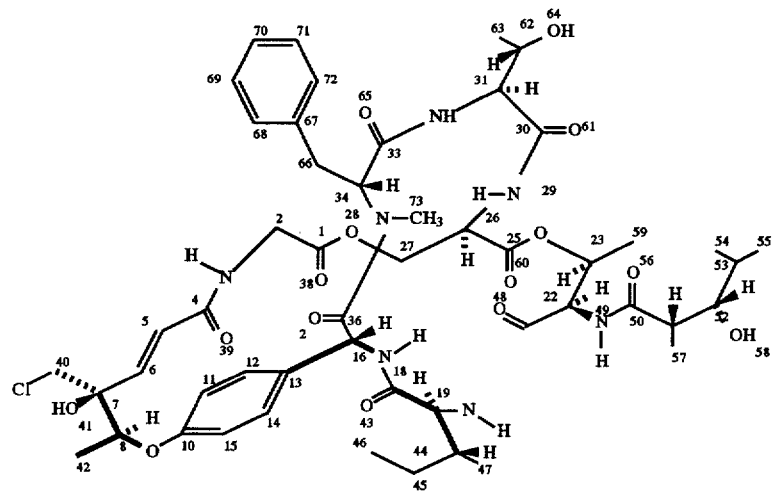

The spectral data for salinamide B is set forth in Table 3.

TABLE 3

Spectral Data for Salinamide B

Source: CNB091, a Streptomyces sp. from a surface swab of a *Cassiopeia xamachana*. Culture maintained at Scripps Institute of Oceanography, University of California at San Diego.
$[\alpha]_D^{-65°}$   mp 239–241° C. melts
Molecular Formula: $C_{51}H_{69}N_7O_{15}Cl$
HRFABMS: (M + H$^+$) m/z 1056.470 (obs), 1056.468 (calc), Δ 1.9 ppm
IR (CDCl3): 3445, 3347, 1745, 1734, 1683, 1651, 1636 cm$^{-1}$
UV (MeOH): 282, 268, 227, 209 nm The NMR data for salinamide B is set forth in Table 4. The carbon numbers in Table 4 correspond to the numbered carbons in the above formula for salinamide B.

TABLE 4

NMR data for salinamide B

| C/X # | δ$^{a13}$C | δ$^{b1}$H | TOCSY$^c$ |
|---|---|---|---|
| 1 | 170.2 (C) | | |
| 2 | 40.7 (CH$_2$) | 4.90 (dd, 18.8, 10.0) | 3, 3.62 |
|   |              | 3.62 (d, 18.8)        | 3, 4.90 |
| 3 |              | 7.02 (bd)             |         |
| 4 | 165.2 (C)    |                       |         |
| 5 | 118.1 (CH)   | 5.92 (d, 15.6)        | 6       |
| 6 | 146.9 (CH)   | 6.30 (d, 15.6)        | 5       |
| 7 | 81.3 (C)     |                       |         |
| 8 | 79.7 (CH)    | 4.78 (m)              | 42      |
| 10 | 160.9 (C)   |                       |         |
| 11 | 123.3† (CH) | 6.9–7.1 (br)          |         |
| 12 | 128.4† (CH) | 6.9–7.1 (br)          |         |
| 13 | 123.0 (C)   |                       |         |
| 14 | 131.1*      | 6.9–7.1 (br)          |         |
| 15 | 124.0† (CH) | 6.9–7.1 (br)          |         |
| 16 | 56.6 (CH)   | 5.05 (d, 2.0)         | 17      |
| 17 |             | 8.71 (bs)             | 16      |
| 19 | 173.7 (C)   |                       |         |
| 20 |             | 6.50 (d, 10.8)        | 19, 44, 47 |
| 21 | 167.8 (C)   |                       |         |
| 22 | 56.2 (CH)   | 4.84 (m)              | 23, 49, 59 |
| 23 | 73.6 (CH)   | 5.44 (dq, 6.4, 2.0)   | 22, 49, 59 |
| 25 | 168.9 (C)   |                       |         |
| 26 | 53.1 (CH)   | 4.68 (bs)             | 27, 29  |
| 27 | 66.5 (CH$_2$) | 4.75 (q, 8.6, 6.0)  | 26, 28, 4.50 |
|    |             | 4.50 (bd, 10.0)       | 26, 28, 4.75 |
| 29 |             | 7.73 (bs)             | 26, 27  |
| 30 | 170.1 (C)   |                       |         |
| 31 | 61.6 (CH)   | 4.38 (d, 7.6)         | 32, 62, 63 |
| 32 |             | 7.23 (bd, 9.6)        | 31      |
| 33 | 170.1 (C)   |                       |         |
| 34 | 69.3 (CH)   | 3.73 (dd, 11.6, 2.0)  | 66      |
| 36 | 170.2 (C)   |                       |         |
| 40 | 47.9 (CH$_2$) | 3.37 (d, 11.2)      | 3.20    |
|    |             | 3.20 (m)              | 3.37    |
| 42 | 14.5 (CH$_3$) | 1.47 (d, 5.6)       | 8       |
| 44 | 39.8 (CH)   | 1.72 (m)              | 19, 20, 45, 46, 47 |
| 45 | 26.3 (CH$_2$) | 1.28 (m)            | 44      |
|    |             | 1.14 (m)              | 44      |
| 46 | 11.5 (CH$_3$) | 0.88 (d, 8.4)       | 44, 45  |
| 47 | 14.4 (CH$_3$) | 0.83 (d, 6.8)       | 19, 20, 44 |
| 49 |             | 7.84 (d, 8.6)         | 22, 23  |
| 50 | 177.9 (C)   |                       |         |
| 51 | 42.1 (CH)   | 2.74 (m)              | 52, 57, 58 |
| 52 | 80.8 (CH)   | 3.19 (m)              | 51, 54, 55, 57, 58 |
| 53 | 32.4 (CH)   | 1.65 (q, 6.4)         | 52, 54, 55, 58 |
| 54 | 18.5 (CH$_3$) | 0.94 (d, 6.4)       | 52, 53, 55, 58 |
| 55 | 19.9 (CH$_3$) | 0.88 (d, 6.6)       | 52, 53, 54, 58 |
| 58 |             | 3.51 (m)              | 51, 52, 53, 54, 55 |
| 59 | 15.8 (CH$_3$) | 1.38 (d, 6.4)       | 22, 23  |
| 62 | 68.9 (CH)   | 4.34 (bq, 7.5)        | 31, 63, 64 |
| 63 | 21.4 (CH$_3$) | 1.64 (d, 6.0)       | 31, 62, 64 |
| 64 |             | 5.90 (bs)             | 63, 64  |
| 66 | 34.8 (CH$_2$) | 3.42 (m)            | 34, 3.23 |
| 67 | 137.7 (C)   |                       |         |
| 68,72 | 129.2 (CH) | 6.91 (d, 6.8)       |         |
| 69,71 | 128.5 (CH) | 6.97 (t, 6.8)       |         |
| 70 | 128.4 (CH)  | 6.99 (d, 6.8)         |         |
| 73 | 40.0 (CH$_3$) | 2.60 (s)            |         |
|    |             | 3.25 (m)              | 34, 3.42 |

$^{a13}$C NMR experiments done at −30° C. in CDCl$_3$ on a VXR500 NMR at 125 MHz, relative to TMS.
$^{b1}$H NMR experiments done at −30° C. (1-D) or room temperature (2-D) in CDCl$_3$ on a VXR500 NMR at 500 MHz, relative to TMS.
$^{c,*}$Shifts may be interchanged.

Figure 4:
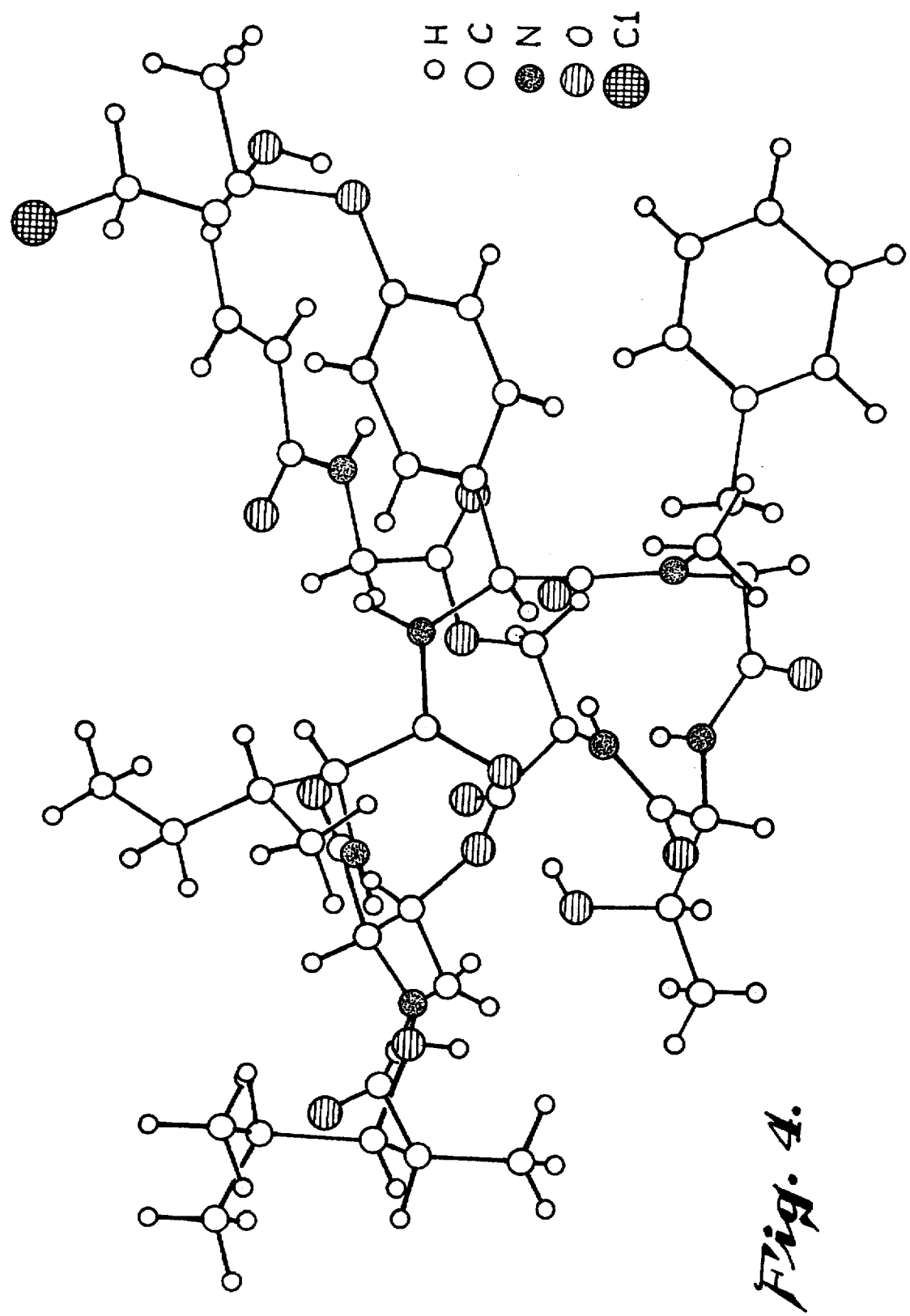
FIG. 4 is an x-ray drawing of salinamide B.
Figure 5:
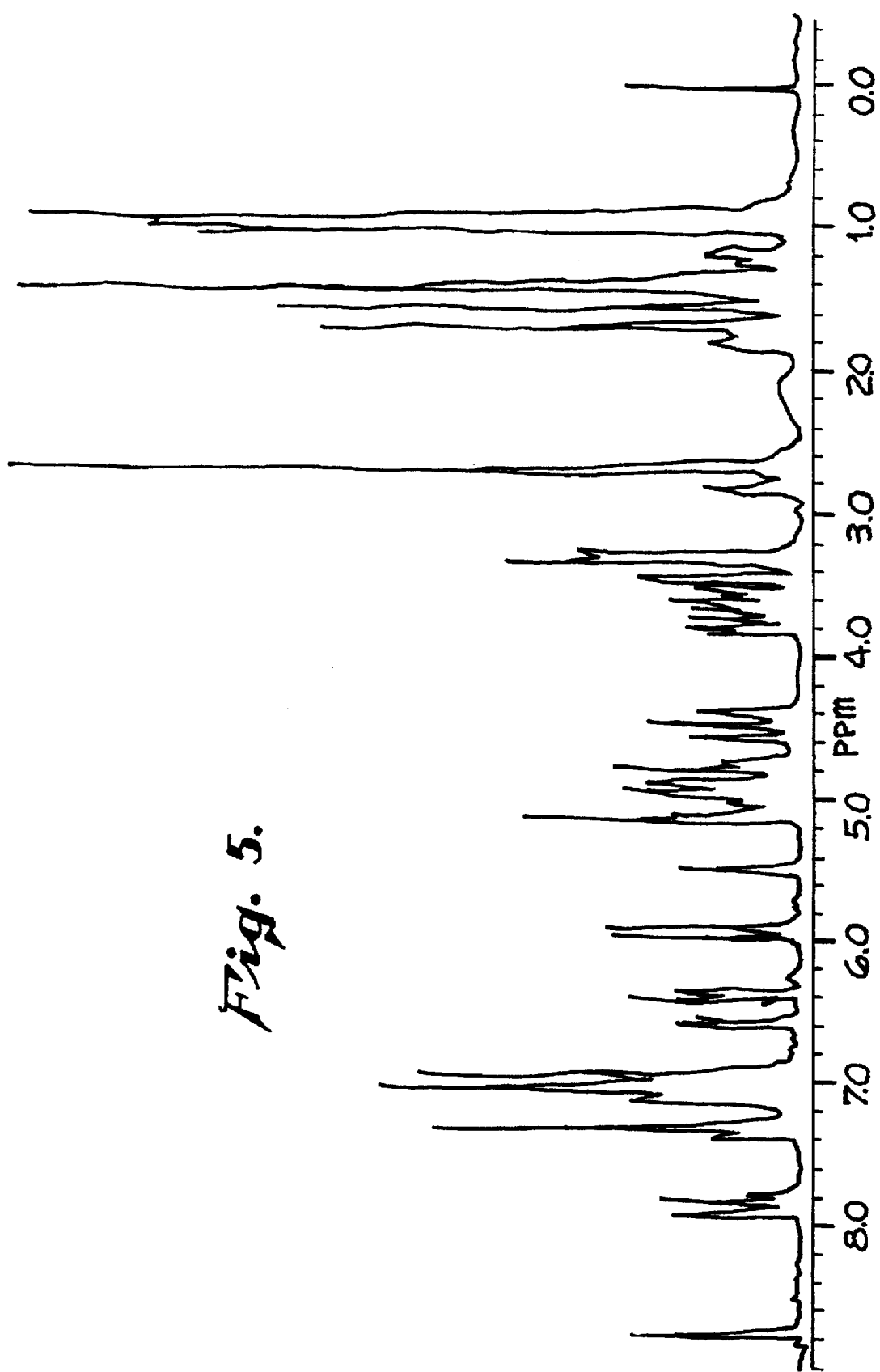
FIG. 5 is a $^1H$ NMR spectra of salinamide B taken at 26° C.

An x-ray drawing of salinamide B is shown in FIG. 4. FIG. 5 is a $^1$H NMR spectra of salinamide B in CDCl$_3$ at 360 MHz at 26° C.

Salinamide A and salinamide B are produced by fermentation of marine bacterium CNB-091 in seawater-based media. CNB-091 is a marine actinomycete which was isolated from the surface of the jellyfish *Cassiopeia xamachana* which is commonly found in the Florida keys. The CNB-091 bacterium was collected from the jellyfish surface utilizing conventional techniques for bacterium isolation. An exemplary technique involves swabbing the surface of *C. xamachana* with a sterile cotton-tipped applicator. The applicator is immersed in 10 ml of sterile seawater, mixed, and the resulting suspension serially diluted ten-fold with sterile seawater. Small volumes (0.05 ml) of each dilution are then inoculated onto the surface of a seawater-based agar medium and spread with a sterile bent glass rod. The CNB-091 forms colonies on the agar surface within 7 to 21 days of inoculation.

CNB-091 is removed with a sterile wire loop from the surface of the inoculated agar medium and streaked on fresh plates until a pure strain is obtained as judged by uniform colony morphology. CNB-091 produces well developed branching mycelium, tan aerial hyphae and spores, and creme-colored vegetative mycelia. Whole cell hydrolysates of strain CNB-091 contain the LL isomer of diaminopimelic acid and the sugars glucose and ribose. This information indicates that CNB-091 is a Streptomyces sp. Further, positive identification of CNB-091 is provided by its ability to produce salinamides A and B when fermented in seawater-based media.

Salinamides A and B are produced by CNB-091 by fermentation in seawater-based media at room temperature. The fermentation media should contain from 70–80 volume percent filtered seawater, 20–30 volume percent deionized water, 0.5 to 1.5 volume percent soluble starch, 0.2 to 0.6 volume percent yeast extract and 0.1 to 0.3 volume percent peptone. An exemplary media will contain about 74 volume percent filtered seawater, 24.4 volume percent deionized water, 1 volume percent soluble starch, 0.4 volume percent yeast extract and 0.2 volume percent peptone.

The fermentation of CNB-091 is accomplished according to conventional seawater media growth procedures. The CNB-091 is typically incubated at room temperature (approximately 26° C.) on a rotary shaker at approximately 200 rpm for about 1 week.

The biologically-purified compositions in accordance with the present invention are prepared by extracting the salinamide A and salinamide B from the fermentation broth. As used in this specification, "biologically-purified" means that the bacteria or salinamide has been extracted or otherwise separated from its naturally occurring condition to form a purified composition which contains the uncontaminated bacteria or salinamide.

The extraction of salinamide A and B from the fermentation broth may be conducted according to any of the conventional separation techniques.

Salinamides A and B can be directly extracted from the fermentation broth by replicate ethylacetate liquid extraction. Salinamides A and B are subsequently isolated from the crude ethylacetate extract by combined chromatographic methods. The extract is first fractionated with a vacuum activated silica gel column. Solvents typically utilized are isooctane ethylacetate mixtures. Fractions rich in salinamides A and B are combined and subjected to high performance liquid chromatography using five micron silica columns operating in semi-preparative mode. Peaks representing pure salinamides A and B are subsequently obtained using 70 to 90 percent ethylacetate-isooctane mixtures. Final purification of salinamides A and B is achieved by appropriate crystallization of the same solvents.

After extraction and separation, salinamides A and B can be positively identified not only by their structure, but also by the identifying characteristics and NMR spectra set forth above and in the Figures.

Salinamides A and/or B have been found to exhibit antibiotic activity against Gram-positive bacteria and topical anti-inflammatory activity. Accordingly, salinamides A and/or B may be used alone or in combination with a pharmaceutically acceptable carrier in the treatment of bacterial infections and tissue inflammation. The carriers used in combination with salinamide A or B can be any of the pharmaceutically acceptable carriers including saline, liposomes, organic based oils, ethanol, glycerol, propylene glycol and the like. Any of the conventional carrier compositions used in combination with antibiotic and anti-inflammatory agents may be suitable. The dosage levels may also be varied depending upon the extent of infection, or inflammation and other factors. Salinamides A and/or B may be applied topically or given intravenously, intramuscularly, intrathecaly and direct injection into joints.

Salinamides A and/or B may also be used in skin cremes. Small amounts of salinamide A and/or B, on the order of a few weight percent, are added to ointments, cremes, emulsions or other suitable skin moisturizing bases. The salinamides A and B may be added to the skin creme in a semi-purified form. Salinamides A and/or B are preferably added to skin cremes which include moisturizers and other conventional skin creme ingredients.

Examples of practice demonstrating the anti-inflammatory effectiveness of salinamides A and B are as follows.

Salinamides A and B were tested by measuring inhibition of phorbol-induced inflammation (edema) of mouse ears. This is a conventional test which has been accepted as demonstrating a compound's effectiveness in reducing inflammation. The compound is topically applied in acetone to the inside pinnae of the ears of mice in a solution containing the edema-causing irritant, i.e. phorbol 12-myristate 13-acetate (PMA). PMA alone (2 microgram per ear) or in combination with varying amounts of salinamide A or salinamide B was applied to the left ears of (5 mice per treatment group). Acetone was applied to all right ears. After a 3-hour and 20-minute incubation at 23° C., the mice were sacrificed, the ears removed and bores taken and weighed. Edema was measured by subtracting the weight of the right ear (acetone control) from the weight of the left ear (treated). The results were recorded as a percent decrease (inhibition) or percent increase (potentiation) in edema relative to the PMA control group edema. The results are summarized in the following tables.

TABLE 5

Inhibition of Mouse Ear Edema - Standard Protocol

| Compound | Dose (ug/ear) | Inhibition |
|---|---|---|
| Salinamide A | 100 | 70.0 |
|  | 50 | 69.9 |
|  | 25 | 19.0 |
|  | 10 | 12.5 |
| Salinamide B | 50 | 81.0 |
|  | 25 | 45.0 |
|  | 10 | 42.0 |
|  | 5 | 14.0 |

Salinamides A and B were also tested to demonstrate their antibiotic activity against Gram-positive bacteria. Imipenem was used as a standard.

The most potent in vitro antibiotic activity demonstrated by salinamides A and B was against *Streptococcus pneumoniae* and *Staphylococcus pyrogenes* with MIC values of 4 microgram per milliliter for salinamide A and 4 and 2 microgram per millimeter for salinamide B.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the above preferred embodiments, but is only limited by the following claims.

What is claimed is:

1. A method for treating mammals having inflamed tissue to reduce inflammation which comprises:

administering to said mammal an inflammation reducing effective amount of a composition comprising a bicyclic depsipeptide selected from the group consisting of salinamide A and salinamide B wherein salinamide A has the structure
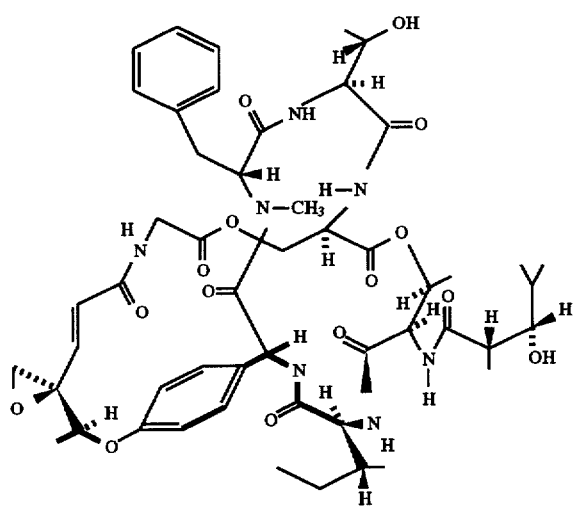
and; wherein salinamide B has the structure
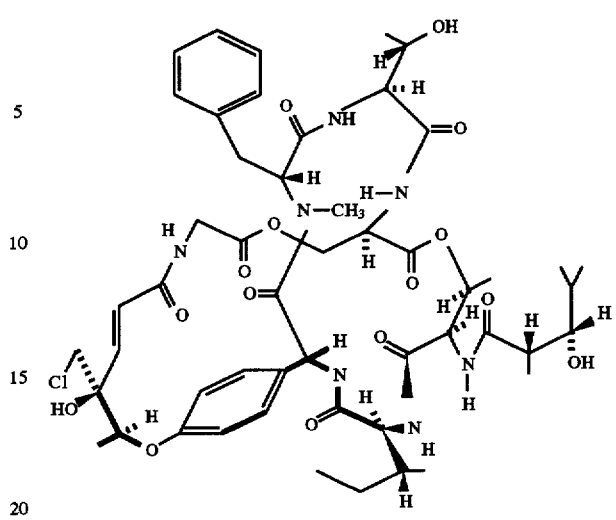
2. A method for treating mammals according to claim 1 wherein said bicyclic depsipeptide is salinamide A.
3. A method for treating mammals according to claim 1 wherein said bicyclic depsipeptide is salinamide B.
* * * * *